(12) United States Patent
Izhikevich

(10) Patent No.: US 9,311,593 B2
(45) Date of Patent: Apr. 12, 2016

(54) APPARATUS AND METHODS FOR POLYCHRONOUS ENCODING AND MULTIPLEXING IN NEURONAL PROSTHETIC DEVICES

(75) Inventor: Eugene M. Izhikevich, San Diego, CA (US)

(73) Assignee: Brain Corporation, San Diego, CA (US)

( * ) Notice: Subject to any disclaimer, the term of this patent is extended or adjusted under 35 U.S.C. 154(b) by 1197 days.

(21) Appl. No.: 13/117,048

(22) Filed: May 26, 2011

(65) Prior Publication Data

US 2012/0303091 A1 Nov. 29, 2012

(51) Int. Cl.
*A61N 1/36* (2006.01)
*G06N 3/04* (2006.01)
*G06F 19/00* (2011.01)

(52) U.S. Cl.
CPC ............ *G06N 3/049* (2013.01); *G06F 19/3406* (2013.01); *G06F 19/36* (2013.01)

(58) Field of Classification Search
None
See application file for complete search history.

(56) References Cited

U.S. PATENT DOCUMENTS

| | | | |
|---|---|---|---|
| 5,063,603 | A | 11/1991 | Burt |
| 5,138,447 | A | 8/1992 | Shen et al. |
| 5,216,752 | A | 6/1993 | Tam |
| 5,272,535 | A | 12/1993 | Elabd |
| 5,355,435 | A | 10/1994 | Deyong et al. |
| 5,638,359 | A | 6/1997 | Peltola et al. |
| 5,673,367 | A | 9/1997 | Buckley |
| 5,875,108 | A | 2/1999 | Hoffberg |
| 6,009,418 | A | 12/1999 | Cooper |
| 6,014,653 | A | 1/2000 | Thaler |
| 6,035,389 | A | 3/2000 | Grochowski |
| 6,418,424 | B1 | 7/2002 | Hoffberg et al. |
| 6,458,157 | B1 | 10/2002 | Suaning |
| 6,509,854 | B1 | 1/2003 | Morita |
| 6,545,705 | B1 | 4/2003 | Sigel et al. |

(Continued)

FOREIGN PATENT DOCUMENTS

| | | |
|---|---|---|
| CN | 102226740 A | 10/2011 |
| JP | 4087423 | 3/1992 |

(Continued)

OTHER PUBLICATIONS

Szatmary et al. Spike-Timing Theory of Working Memory. PLoS Computational Biology. vol. 6, Issue 8. Aug. 19, 2010 [retrieved on Aug. 19, 2012]. Retrieved from the Internet: <URL: http://www.ploscompbiol.org/article/info%3Adoi%2F10.1371%2Fjournal.pcbi.1000879#>.

(Continued)

*Primary Examiner* — Erica Lee
(74) *Attorney, Agent, or Firm* — Gazdzinski & Associates, PC

(57) ABSTRACT

Apparatus and methods for encoding sensory input information into patterns of pulses and message multiplexing. In one implementation, the patterns of pulses are polychronous (time-locked by not necessary synchronous), and a retinal prosthetic encodes the input signal into the polychronous patterns for delivery via stimulating electrodes. Different polychronous patterns simultaneously encode different sensory signals; (such as different features of the image), thus providing for message multiplexing. Increasing data transmission capacity allows for a reduction in the number of electrodes required for data transmission. In one implementation, an adaptive feedback mechanism is employed to facilitate encoder operation. In another aspect, a computer vision system is described.

24 Claims, 8 Drawing Sheets

(56) References Cited

U.S. PATENT DOCUMENTS

| | | | |
|---|---|---|---|
| 6,545,708 B1 | 4/2003 | Tamayama | |
| 6,546,291 B2 | 4/2003 | Merfeld et al. | |
| 6,581,046 B1 | 6/2003 | Ahissar | |
| 6,625,317 B1 | 9/2003 | Gaffin et al. | |
| 7,565,203 B2* | 7/2009 | Greenberg et al. | 607/54 |
| 7,580,907 B1 | 8/2009 | Rhodes | |
| 7,653,255 B2 | 1/2010 | Rastogi | |
| 7,737,933 B2 | 6/2010 | Yamano et al. | |
| 7,765,029 B2 | 7/2010 | Fleischer et al. | |
| 7,849,030 B2 | 12/2010 | Ellingsworth | |
| 8,000,967 B2 | 8/2011 | Taleb | |
| 8,015,130 B2 | 9/2011 | Matsugu | |
| 8,103,602 B2 | 1/2012 | Izhikevich | |
| 8,160,354 B2 | 4/2012 | Paquier | |
| 8,200,593 B2 | 6/2012 | Guillen | |
| 8,311,965 B2 | 11/2012 | Breitwisch | |
| 8,315,305 B2 | 11/2012 | Petre | |
| 8,390,707 B2 | 3/2013 | Yamashita | |
| 8,416,847 B2 | 4/2013 | Roman | |
| 8,467,623 B2 | 6/2013 | Izhikevich | |
| 8,583,286 B2 | 11/2013 | Fleischer et al. | |
| 8,712,941 B2 | 4/2014 | Izhikevich et al. | |
| 2002/0038294 A1 | 3/2002 | Matsugu | |
| 2003/0050903 A1 | 3/2003 | Liaw | |
| 2003/0216919 A1 | 11/2003 | Roushar | |
| 2003/0222987 A1* | 12/2003 | Karazuba | 348/207.99 |
| 2004/0136439 A1 | 7/2004 | Dewberry | |
| 2004/0170330 A1 | 9/2004 | Fogg | |
| 2004/0193670 A1 | 9/2004 | Langan et al. | |
| 2005/0015351 A1 | 1/2005 | Nugent | |
| 2005/0036649 A1 | 2/2005 | Yokono et al. | |
| 2005/0283450 A1 | 12/2005 | Matsugu | |
| 2006/0094001 A1 | 5/2006 | Torre | |
| 2006/0129728 A1 | 6/2006 | Hampel | |
| 2006/0161218 A1 | 7/2006 | Danilov | |
| 2007/0022068 A1 | 1/2007 | Linsker | |
| 2007/0176643 A1 | 8/2007 | Nugent | |
| 2007/0208678 A1 | 9/2007 | Matsugu | |
| 2008/0100482 A1 | 5/2008 | Lazar | |
| 2008/0199072 A1 | 8/2008 | Kondo | |
| 2008/0237446 A1 | 10/2008 | Oshikubo | |
| 2009/0043722 A1 | 2/2009 | Nugent | |
| 2009/0287624 A1 | 11/2009 | Rouat et al. | |
| 2010/0036457 A1 | 2/2010 | Sarpeshkar | |
| 2010/0081958 A1 | 4/2010 | She | |
| 2010/0086171 A1 | 4/2010 | Lapstun | |
| 2010/0100482 A1 | 4/2010 | Hardt | |
| 2010/0166320 A1 | 7/2010 | Paquier | |
| 2010/0225824 A1 | 9/2010 | Lazar | |
| 2010/0235310 A1 | 9/2010 | Gage et al. | |
| 2010/0299296 A1 | 11/2010 | Modha et al. | |
| 2011/0016071 A1 | 1/2011 | Guillen | |
| 2011/0119214 A1 | 5/2011 | Breitwisch | |
| 2011/0119215 A1 | 5/2011 | Elmegreen | |
| 2011/0137843 A1 | 6/2011 | Poon et al. | |
| 2011/0160741 A1 | 6/2011 | Asano | |
| 2012/0011090 A1 | 1/2012 | Tang | |
| 2012/0083982 A1 | 4/2012 | Bonefas | |
| 2012/0084240 A1 | 4/2012 | Esser et al. | |
| 2012/0109866 A1 | 5/2012 | Modha | |
| 2012/0303091 A1 | 11/2012 | Izhikevich | |
| 2012/0308076 A1 | 12/2012 | Piekniewski | |
| 2012/0308136 A1 | 12/2012 | Izhikevich | |
| 2013/0073484 A1 | 3/2013 | Izhikevich | |
| 2013/0073491 A1 | 3/2013 | Izhikevich | |
| 2013/0073492 A1 | 3/2013 | Izhikevich | |
| 2013/0073495 A1 | 3/2013 | Izhikevich | |
| 2013/0073496 A1 | 3/2013 | Szatmary | |
| 2013/0073498 A1 | 3/2013 | Izhikevich | |
| 2013/0073499 A1 | 3/2013 | Izhikevich | |
| 2013/0073500 A1 | 3/2013 | Szatmary | |
| 2013/0151450 A1 | 6/2013 | Ponulak | |
| 2013/0218821 A1 | 8/2013 | Szatmary | |
| 2013/0251278 A1 | 9/2013 | Izhikevich | |
| 2013/0297539 A1 | 11/2013 | Piekniewski et al. | |
| 2013/0297541 A1 | 11/2013 | Piekniewski et al. | |
| 2013/0297542 A1 | 11/2013 | Piekniewski et al. | |
| 2013/0325766 A1 | 12/2013 | Petre et al. | |
| 2013/0325768 A1 | 12/2013 | Sinyavskiy | |
| 2013/0325773 A1 | 12/2013 | Sinyavskiy | |
| 2013/0325774 A1 | 12/2013 | Sinyavskiy | |
| 2013/0325775 A1 | 12/2013 | Sinyavskiy | |
| 2013/0325777 A1 | 12/2013 | Petre et al. | |
| 2014/0012788 A1 | 1/2014 | Piekniewski | |
| 2014/0016858 A1 | 1/2014 | Richert | |
| 2014/0032458 A1 | 1/2014 | Sinyavskiy | |
| 2014/0032459 A1 | 1/2014 | Sinyavskiy | |
| 2014/0052679 A1 | 2/2014 | Sinyavskiy | |
| 2014/0064609 A1 | 3/2014 | Petre et al. | |
| 2014/0122397 A1 | 5/2014 | Richert | |
| 2014/0122398 A1 | 5/2014 | Richert | |
| 2014/0122399 A1 | 5/2014 | Szatmary | |
| 2014/0156574 A1 | 6/2014 | Piekniewski | |

FOREIGN PATENT DOCUMENTS

| | | |
|---|---|---|
| JP | 4087423 A | 3/1992 |
| RU | 2108612 C1 | 10/1998 |
| RU | 2406105 C2 | 12/2010 |
| RU | 2424561 C2 | 7/2011 |
| WO | 2008083335 A2 | 7/2008 |
| WO | 2008132066 A1 | 11/2008 |

OTHER PUBLICATIONS

Berkes and Wiskott. Slow feature analysis yields a rich repertoire of complex cell properties. *Journal of Vision* (2005) vol. 5 (6).

Bohte, 'Spiking Nueral Networks' Doctorate at the University of Leiden, Holland, Mar. 5, 2003, pp. 1-133 [retrieved on Nov. 14, 2012]. Retrieved from the internet: <URL: http://holnepagcs, cwi ,n11-sbolltedmblica6ond)hdthesislxif>.

Brette et al., Brian: a simple and flexible simulator for spiking neural networks, The Neuromorphic Engineer, Jul. 1, 2009, pp. 1-4, doi: 10.2417/1200906.1659.

Cessac et al. 'Overview of facts and issues about neural coding by spikes.' Journal of Physiology, Paris 104.1 (2010): 5.

Cuntz et al., 'One Rule to Grow Them All: A General Theory of Neuronal Branching and Its Paractical Application' PLOS Computational Biology, 6 (8), Published Aug. 5, 2010.

Davison et al., PyNN: a common interface for neuronal network simulators, Frontiers in Neuroinformatics, Jan. 2009, pp. 1-10, vol. 2, Article 11.

Djurfeldt, Mikael, The Connection-set Algebra: a formalism for the representation of connectivity structure in neuronal network models, implementations in Python and C++, and their use in simulators BMC Neuroscience Jul. 18, 2011 p. 1 12(Suppl 1):P80.

Dorval et al., 'Probability distributions of the logarithm of inter-spike intervals yield accurate entropy estimates from small datasets.' Journal of neuroscience methods 173.1 (2008): 129.

Fidjeland et al., Accelerated Simulation of Spiking Neural Networks Using GPUs [online],2010 [retrieved on Jun. 15, 2013], Retrieved from the Internet: URL:http://ieeexplore.ieee.org/xpls/abs_all.jsp?ammber=5596678&tag=1.

Field, G.; Chichilnisky, E. Information Processing in the Primate Retina: Circuitry and Coding. *Annual Review of Neuroscience*, 2007, 30(1), 1-30.

Fiete, et al. Spike-Time-Dependent Plasticity and Heterosynaptic Competition Organize Networks to Produce Long Scale-Free Sequences of Neural Activity. *Neuron* 65, Feb. 25, 2010, pp. 563-576.

Floreano et al., 'Neuroevolution: from architectures to learning' Evol. Intel. Jan. 2008 1:47-62, [retrieved Dec. 30, 2013] [retrieved online from URL:<http://inforscience.epfl.ch/record/112676/files/FloreanoDuerrMattiussi2008.p df>.

Földiák, P. Learning invariance from transformation sequences. *Neural Computation*, 1991, 3(2), 194-200.

Froemke et al., Temporal modulation of spike-timing-dependent plasticity, Frontiers in Synaptic Neuroscience, vol. 2, Article 19, pp. 1-16 [online] Jun. 2010 [retrieved on Dec. 16, 2013]. Retrieved from the internet: <frontiersin.org>.

(56) References Cited

OTHER PUBLICATIONS

Gerstner et al. (1996) A neuronal learning rule for sub-millisecond temporal coding. *Nature* vol. 383 (6595) pp. 76-78.
Gewaltig et al., 'NEST (Neural Simulation Tool)', Scholarpedia, 2007, pp. 1-15, 2(4): 1430, doi: 1 0.4249/scholarpedia.1430.
Gleeson et al., NeuroML: A Language for Describing Data Driven Models of Neurons and Networks with a High Degree of Biological Detail, PLoS Computational Biology, Jun. 2010, pp. 1-19 vol. 6 Issue 6.
Gluck, Stimulus Generalization and Representation in Adaptive Network Models of Category Learning [online], 1991 [retrieved on Aug. 24, 2013]. Retrieved from the Internet:<URL:http:// www.google.com/url?sa=t&rct=j&q=Giuck+%22STIMULUS+GENERALIZATION+AND+REPRESENTATION+IN+ADAPTIVE+NETWORK+MODELS+OF+CATEGORY+LEARN ING%22+ 1991.
Gollisch et al. 'Rapid neural coding in the retina with relative spike latencies.' Science 319.5866 (2008): 11 08-1111.
Goodman et al., Brian: a simulator for spiking neural networks in Python, Frontiers in Neuroinformatics, Nov. 2008, pp. 1-10, vol. 2, Article 5.
Gorchetchnikov et al., NineML: declarative, mathematically-explicit descriptions of spiking neuronal networks, Frontiers in Neuroinformatics, Conference Abstract: 4th INCF Congress of Neuroinformatics, doi: 10.3389/conf.fninf.2011.08.00098.
Graham, Lyle J., The Surf-Hippo Reference Manual, http:// www.neurophys.biomedicale.univparis5. fr/-graham/surf-hippo-files/Surf-Hippo%20Reference%20Manual.pdf, Mar. 2002, pp. 1-128.
Hopfield JJ (1995) Pattern recognition computation using action potential timing for stimulus representation. *Nature* 376: 33-36.
Izhikevich E. M. and Hoppensteadt F.C. (2009) Polychronous Wavefront Computations. *International Journal of Bifurcation and Chaos*, 19:1733-1739.
Izhikevich E.M. (2004) Which Model to Use for Cortical Spiking Neurons? *IEEE Transactions on Neural Networks*, 15:1063-1070.
Izhikevich E.M. (2006) Polychronization: Computation With Spikes. *Neural Computation*,18:245-282.
Izhikevich et al., 'Relating STDP to BCM', Neural Computation (2003) 15, 1511-1523.
Izhikevich, E.M. (2007) Dynamical Systems in Neuroscience: The Geometry of Excitability and Bursting, *The MIT Press*, 2007.
Izhikevich, 'Simple Model of Spiking Neurons', IEEE Transactions on Neural Networks, vol. 14, No. 6, Nov. 2003, pp. 1569-1572.
Janowitz, M.K.; Van Rossum, M.C.W. Excitability changes that complement Hebbian learning. *Network, Computation in Neural Systems*. 2006, 17 (1), 31-41.
Karbowski et al., 'Multispikes and Synchronization in a Large Neural Network with Temporal Delays', Neural Computation 12, 1573-1606 (2000).
Khotanzad, Alireza, Classification of invariant image representations using a neural network, IEEF. Transactions on Acoustics, Speech, and Signal Processing vol. 38 No. 6 Jun. 1990 pp. 1028-1038.
Khotanzad, 'Classification of invariant image representations using a neural network' IEEF. Transactions on Acoustics, Speech, and Signal Processing, vol. 38, No. 6, Jun. 1990, pp. 1028-1038 [online], [retrieved on Dec. 10, 2013]. Retrieved from the Internet <URL: http://www-ee.uta.edu/eeweb/IP/Courses/SPR/Reterence/Khotanzad.pdf>.
Knoblauch, et al. Memory Capacities for Synaptic and Structural Plasticity, *Neural Computation* 2009, pp. 1-45.
Laurent, 'Issue 1—nnql—Refactor Nucleus into its own file—Neural Network Query Language' [retrieved on Nov. 12, 2013]. Retrieved from the Internet: <URL:https:// code.google.com/p/nnql/issues/detail?id=1.
Laurent, 'The Neural Network Query Language (NNQL) Reference' [retrieved on Nov. 12, 2013]. Retrieved from the Internet: <URL'https://code.google.com/p/nnql/issues/detail?id=1>.
Lazar et al. 'A video time encoding machine', in Proceedings of the 15th IEEE International Conference on Image Processing (ICIP '08}, 2008, pp. 717-720.

Lazar et al. 'Consistent recovery of sensory stimuli encoded with MIMO neural circuits.' Computational intelligence and neuroscience (2010): 2.
Lazar et al. 'Multichannel time encoding with integrate-and-fire neurons.' Neurocomputing 65 (2005): 401-407.
Masquelier and Thorpe. Learning to recognize objects using waves of spikes and Spike Timing-Dependent Plasticity. *Neural Networks* (IJCNN). *The 2010 International Joint Conference* on DOI—10.1109/IJCNN.2010.5596934 (2010) pp. 1-8.
Masquelier, Timothee. 'Relative spike time coding and STOP-based orientation selectivity in the early visual system in natural continuous and saccadic vision: a computational model.' Journal of computational neuroscience 32.3 (2012): 425-441.
Meister, M. Multineuronal codes in retinal signaling. *Proceedings of the National Academy of sciences*. 1996, 93, 609-614.
Meister, M.; Berry, M.J. The neural code of the retina, *Neuron*. 1999, 22, 435-450.
Nichols, A Re configurable Computing Architecture for Implementing Artificial Neural Networks on FPGA, Master's Thesis, The University of Guelph, 2003, pp. 1-235.
Oster M., Lichtsteiner P., Delbruck T, Liu S. A Spike-Based Saccadic Recognition System. *ISCAS 2007. IEEE International Symposium on Circuits and Systems*, 2009, pp. 3083-3086.
Paugam-Moisy et al. 'Computing with spiking neuron networks.' Handbook of Natural Computing, 40 p. Springer, Heidelberg (2009).
Paugam-Moisy et al., "Computing with spiking neuron networks" G. Rozenberg T. Back, J. Kok (Eds.), Handbook of Natural Computing, Springer-Verlag (2010) [retrieved Dec. 30, 2013], [retrieved online from link.springer.com].
Pavlidis et al. Spiking neural network training using evolutionary algorithms, In: Proceedings 2005 IEEE International Joint Conference on Neural Networkds, 2005. IJCNN'05, vol. 4, pp. 2190-2194 Publication Date Jul. 31, 2005 [online] [Retrieved on Dec. 10, 2013] Retrieved from the Internet <URL: http://citeseerx.ist.psu.edu/viewdoc/download?doi=10.1.1.5.4346&rep=rep1&type=pdf.
Rekeczky, et al., "Cellular Multiadaptive Analogic Architecture: A Computational Framework for UAV Applications." May 2004.
Revow M., Williams C., and Hinton, G.E., 1996, Using Generative Models for Handwritten Digit Recognition, *IEEE Trans. on Pattern Analysis and Machine Intelligence*, 18, No. 6, Jun. 1996.
Sanchez, Efficient Simulation Scheme for Spiking Neural Networks, *Doctoral Thesis*, Universita di Granada Mar. 28, 2008, pp. 1-104.
Sato et al., 'Pulse interval and width modulation for video transmission.' Cable Television, IEEE Transactions on 4 (1978): 165-173.
Schemmel, J., et al. Implementing synaptic plasticity in a VLSI spiking neural network model, Proceedings of the 2006 International Joint Conference on Neural Networks, Jul. 2006 pp. 1-6.
Schnitzer, M.J.; Meister, M.; Multineuronal Firing Patterns in the Signal from Eye to Brain. *Neuron*, 2003, 37, 499-511.
Serrano-Gotarredona, et al, "On Real-Time: AER 2-D Convolutions Hardware for Neuromorphic Spike-based Cortical Processing", Jul. 2008.
Simulink.RTM. model [online], [Retrieved on Dec. 10, 2013] Retrieved from <URL: http://www.mathworks.com/ products/simulink/index.html>.
Sinyavskiy et al. 'Reinforcement learning of a spiking neural network in the task control of an agent in a virtual discrete environment' Rus. J. Nonlin. Dyn., 2011, vol. 7, No. 4 (Mobile Robots), pp. 859-875, chapters 1-8 (Russian Article with English Abstract).
Sjostrom et al., 'Spike-Timing Dependent Plasticity' Scholarpedia, 5(2):1362 (2010), pp. 1-18.
Szatmary et al., 'Spike-timing Theory of Working Memory' PLoS Computational Biology, vol. 6, Issue 8, Aug. 19, 2010 [retrieved on Dec. 30, 2013]. Retrieved from the Internet: <URL: http://www.ploscompbiol.org/article/info%3Adoi% 2F10.1371 %2Fjournal.pcbi.10008 79#>.
Thomas S. and Riesenhuber, M, 2004, Realistic Modeling of Simple and Complex Cell Tuning in the HMAX Model, and Implications for Invariant Object Recognition in Cortex, *Al Memo* 2004-017 Jul. 2004.

(56) References Cited

OTHER PUBLICATIONS

Thorpe, S.J., Delorme, A. & VanRullen, R. (2001). Spike-based strategies for rapid processing. *Neural Networks* 14, pp. 715-725.

Thorpe, S.J., Guyonneau, R., Guilbaud, N., Allegraud, J-M. & VanRullen, R. (2004). SpikeNet: real-time visual processing with one spike per neuron. *Neurocomputing*, 58-60, pp. 857-864.

Tim Gollisch and Markus Meister (2008) Rapid Neural Coding in the Retina with Relative Spike Latencies. *Science* 319:1108-1111.

Van Rullen R.; Thorpe, S. Rate Coding versus temporal order coding: What the Retinal ganglion cells tell the visual cortex. *Neural computation*, 2001, 13, 1255-1283.

VanRullen, R. & Koch, C. (2003). Is perception discrete or continuous? *Trends in Cognitive Sciences* 7(5), pp. 207-213.

VanRullen, R., Guyonneau, R. & Thorpe, S.J. (2005). Spike times make sense. *Trends in Neurosciences* 28(1).

Wallis, G.; Rolls, E. T. A model of invariant object recognition in the visual system. *Progress in Neurobiology*. 1997, 51, 167-194.

Wang 'The time dimension for scene analysis.' Neural Networks, IEEE Transactions on 16.6 (2005): 1401-1426.

Wiskott, L.; Sejnowski, T.J. Slow feature analysis: Unsupervised learning of invariances. *Neural Computation*, 2002, 14, (4), 715-770.

Zarandy, et al., "Bi-i: A Standalone Ultra High Speed Cellular Vision System", Jun. 2005.

* cited by examiner

APPARATUS AND METHODS FOR POLYCHRONOUS ENCODING AND MULTIPLEXING IN NEURONAL PROSTHETIC DEVICES

CROSS-REFERENCE TO RELATED APPLICATIONS

This application is related to co-owned U.S. Provisional Patent Application No. 61/318,191, filed Mar. 26, 2010 and entitled "Systems and Method for Invariant Pulse Latency Coding", U.S. patent application Ser. No. 12/869,573, filed Aug. 26, 2010 and entitled "Systems and Methods for Invariant Pulse Latency Coding", now issued as U.S. Pat. No. 8,315,305 on Nov. 20, 2012, U.S. patent application Ser. No. 12/869,583, filed Aug. 26, 2010 and entitled "Invariant Pulse Latency Coding Systems and Methods", now issued as U.S. Pat. No. 8,467,623 on Jun. 18, 2013, each of the foregoing incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

1. Field of the Invention

The present invention relates generally to visual encoding in a computerized processing system, and more particularly in one exemplary aspect to a computer vision apparatus and methods of encoding of visual information for vision prosthetic devices.

2. Description of Related Art

In a vertebrate vision system, the retina is a light sensitive tissue lining the inner surface of the eye. Light falling upon the retina triggers nerve impulses that are sent to visual centers of the brain via fibers of the optic nerve. The optic fibers from the retina to the thalamus represent a visual information bottleneck. The retina, consisting of millions of photoreceptors, is coupled to millions of neurons in the primary visual cortex to process visual information, yet there are only hundreds of thousands of retinal ganglion cells giving rise to the optic fibers that connect retina to the brain.

When retinal photoreceptors are damaged, a retinal prosthetic device (e.g., a semiconductor chip) is utilized to encode visual information, and transmit it to the retinal ganglion cells (RGC) via stimulating electrodes. In this case, the number of electrodes (typically limited to tens or hundreds per chip) acts as the information bottleneck that limits the transmission bandwidth and hence the resolution of the perceived image. Presently available retinal prosthetic devices use a small number of individual light sensors directly coupled to the RGCs via individual stimulating electrodes. The sensors are typically arranged into a square pattern (e.g., 3×3 pattern in the exemplary retinal prosthetic manufactured by Second Sight Medical Products, Inc.), and are configured to operate independently from one another by generating electrical pulses in the electrodes in response to light stimulation. The electric pulses evoke firings of the RGCs to mimic their natural firing patterns. It is an open question on what is the optimal firing pattern of RGCs to encode visual signals in a retinal prosthetic device.

Existing models used for retinal prosthetic signal encoding utilize rate encoding; the RGCs are stimulated with pulses of currents of various amplitudes or durations (or waveforms) so to make RGCs fire with various firing rates. This is in line with the common neuroscience theory that the frequency of random firing of retinal ganglion cells (and not the precise timing of pulses) is used to transmit the information to the brain (see, e.g., Field, G.; Chichilnisky, E. Information Processing in the Primate Retina: Circuitry and Coding. *Annual Review of Neuroscience,* 2007, 30(1), 1-30). In another existing approach (see Van Rullen R.; Thorpe, S. Rate Coding versus temporal order coding: What the Retinal ganglion cells tell the visual cortex. *Neural computation,* 2001, 13, 1255-1283), a coding scheme is suggested where each retinal ganglion cell encodes information into pulse timing (or latency) that is measured with respect to a reference timing signal (e.g., the onset of the image). Here, the RGC with the strongest signal fires first, the RGC with the second strongest signal fires next, and so on. Each RGC fires only once.

In both cases (i.e., rate coding and latency coding), each RGC encodes the photoreceptor signal (or other features of the image) into a single analog value (rate or latency), and RGCs encode their values independently. That is, the message transmitted along one RGC is the same regardless of the activities of the other RGCs.

In a different approach described in e.g., Meister, M. Multineuronal codes in retinal signaling. *Proceedings of the National Academy of sciences.* 1996, 93, 609-614, Meister, M; Berry M. J. II. The neural code of the retina. *Neuron.* 1999, 22, 435-450, and Schnitzer, M. J.; Meister, M.; Multineuronal Firing Patterns in the Signal from Eye to Brain. *Neuron,* 2003, 37, 499-511, encoding and multiplexing of visual information into patterns of synchronous pulses involving multiple cells is performed. The advantage of such neuronal code is higher information transmission capacity, as it allows for multiplexing of various photoreceptor signals into pulsed output of multiple RGCs. For example, 4 photoreceptor signals or features, 1, 2, 3, and 4, can be encoded into 3 RGC synchronous firings 1→(1,0,0), 2→(0,1,0), 3→(0,0,1), and 4→(1,1,0), where 1 represents the corresponding RGC firing, and 0 represents a quiescent state. When photoreceptors 1 and 3 are active, the output is a superposition 1+3→(1,0,1), resulting in multiplexing. However, when too many photoreceptors are active, the output consists of a synchronous barrage of pulses (e.g., (1,1,1)) and the information is lost.

All existing approaches have limited information transmission capacity, at least in part because they (i) do not fully utilize multichannel patterns of pulses to encode visual signals, and (ii) do not fully take advantage of the brain's ability to learn to decode such patterns. Accordingly, there is a salient need for a more efficient and scalable visual encoding solution that utilizes data compression at a retinal level prior to data transmission to the brain, in order to among other things, increase resolution capabilities of the retinal prosthetic devices.

SUMMARY OF THE INVENTION

The present invention satisfies the foregoing needs by providing, inter alia, apparatus and methods for polychronous encoding and multiplexing in, e.g., neuronal prosthetic devices.

In one aspect of the invention, an apparatus configured to transmit a signal to a vertebrate nervous system is disclosed.

In one embodiment, the apparatus comprises: a processor configured to receive an input signal representative of at least a portion of a visual frame, an encoder configured to encode the input signal into a plurality of pulses, and a plurality of stimulating electrodes. In one variant, at least a subset of the plurality of pulses is configured in a polychronous pattern comprising at least two non-synchronous pulses. Information related to at least the portion of the visual frame is encoded into the polychronous pattern, and the polychronous pattern is characterized by a group delay that is common to all pulses within the plurality of pulses. The group delay is determined in one implementation by a spatiotemporal filter applied to the input signal, and the polychronous pattern is adapted for transmission via a plurality of electrodes operably coupled to the nervous system.

In another aspect of the invention, a sensory input encoding apparatus is disclosed. In one embodiment, the apparatus comprises a processing apparatus configured to receive and encode the sensory input, comprising information indicative of an object characteristic, into a plurality of pulses such that at least a portion of the plurality of pulses is configured in a first polychronous pattern comprising at least two non-synchronous pulses.

In one variant, the sensory input comprises a visual input signal comprising a frame of pixels.

In another variant, the first polychronous pattern is characterized by a group delay that is common to all pulses within the plurality of pulses, the group delay configured based at least in part on the visual input signal such that the first polychronous pattern is characterized by a group delay that is common to all pulses within the plurality of pulses. The group delay is based in one implementation at least in part on an output generated by a spatiotemporal filter using the visual input signal.

In another variant, the first polychronous pattern is generated responsive to a trigger such as: (i) a temporal event; (ii) receipt of the sensory input; (iii) an appearance of the object in the sensory input; and/or (iv) a timer event.

In yet another variant, the first polychronous pattern is adapted for transmission via a plurality of transmission channels such that at least a subset of the plurality of transmission channels is associated with a channel delay configured to effect a coincident arrival of the at least two non-synchronous pulses at a decoder, and the channel delay is configured based at least in part on the first polychronous pattern.

In still another variant, at least a subset of the plurality of the transmission channels is configurable based on a second polychronous pattern generated prior to the first polychronous pattern.

In a third aspect of the invention, a sensory prosthetic apparatus is disclosed. In one embodiment, the apparatus comprises: an encoder configured to receive a sensory input, and to encode the sensory input into a plurality of pulses configured in a polychronous pattern comprising at least two non-synchronous pulses, and to transmit the plurality of pulses via a plurality of transmission channels, such that each of the plurality of the transmission channels is configured for operable coupling to a receptor.

In one variant, the receptor is configured to interface to at least a portion of a vertebrate nervous system, and the apparatus comprises a retinal prosthetic device.

In another variant, the receptor is configured to interface to a retinal ganglion cell.

In yet another variant, the encoder is configurable to be adaptively adjusted based at least in part on a feedback signal provided by the host of the sensory prosthetic apparatus. Encoding of the sensory input into the plurality of pulses is characterized by at least one parameter, and the encoder adaptive adjustment is configured to modify the at least one parameter.

In a fourth aspect of the invention, a method of encoding sensory input for use in a processing apparatus is disclosed. In one embodiment, the method comprises receiving the sensory input comprising information indicative of an object characteristic, encoding the sensory input into a plurality of pulses, configuring at least a portion of the plurality of pulses in a first polychronous pattern comprising at least two non-synchronous pulses.

In one variant, the sensory input comprises a visual input signal, and the first polychronous pattern is characterized by a group delay that is common to all pulses within the plurality of pulses, the group delay configured based at least in part on the visual input signal.

In another variant, the group delay is configured based at least in part on an output generated by a spatiotemporal filter responsive to the visual input signal.

In another aspect of the invention, an image processing system is disclosed. In one embodiment, the system comprises a processor configured to execute instructions maintained in a storage medium; the instructions cause the processor to encode and multiplex visual signals in neuronal prosthetic devices.

Further features of the present invention, its nature and various advantages will be more apparent from the accompanying drawings and the following detailed description.

Figure 1:
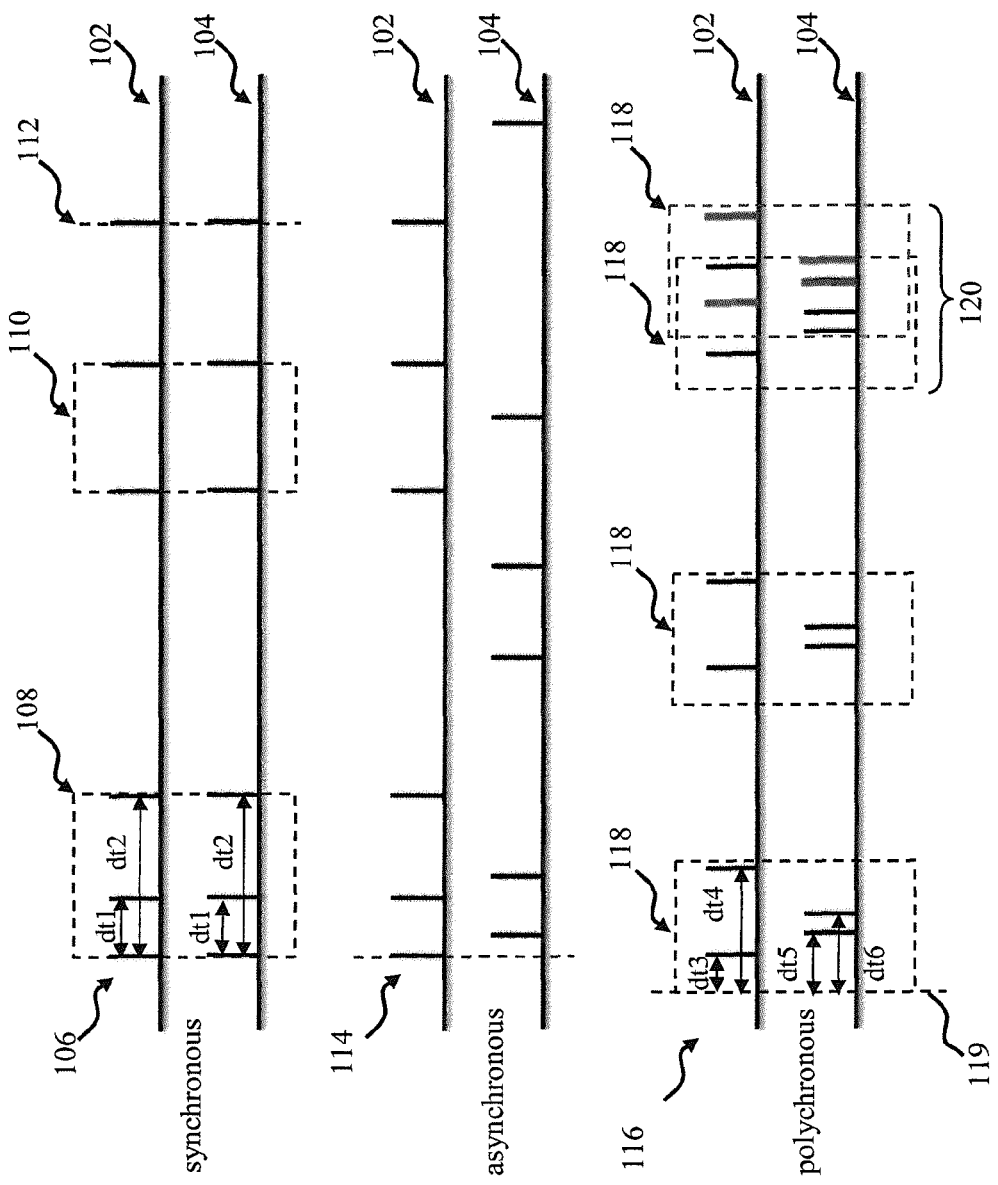
FIG. 1 is a graphical illustration of synchronous, asynchronous and polychronous pulse groups.

All Figures disclosed herein are ©Copyright 2011 Brain Corporation. All rights reserved.

DETAILED DESCRIPTION OF THE INVENTION

Embodiments of the present invention will now be described in detail with reference to the drawings, which are provided as illustrative examples so as to enable those skilled in the art to practice the invention. Notably, the figures and examples below are not meant to limit the scope of the present invention to a single embodiment; other embodiments are possible by way of interchange of, or combination with, some or all of the described or illustrated elements. Wherever convenient, the same reference numbers will be used throughout the drawings to refer to same or like parts.

Where certain elements of these embodiments can be partially or fully implemented using known components, only those portions of such known components that are necessary for an understanding of the present invention will be described, and detailed descriptions of other portions of such known components will be omitted so as not to obscure the invention.

In the present specification, an embodiment showing a singular component should not be considered limiting; rather, the invention is intended to encompass other embodiments including a plurality of the same component, and vice-versa, unless explicitly stated otherwise herein.

Further, the present invention encompasses present and future known equivalents to the components referred to herein by way of illustration.

As used herein, the terms "computer", "computing device", and "computerized device", include, but are not limited to, mainframe computers, workstations, servers, personal computers (PCs) and minicomputers, whether desktop, laptop, or otherwise, personal digital assistants (PDAs), handheld computers, embedded computers, programmable logic devices, digital signal processor systems, personal communicators, tablet computers, portable navigation aids, J2ME equipped devices, cellular telephones, smartphones, personal integrated communication or entertainment devices, neuro-computers, neuromorphic chips, or literally any other device capable of executing a set of instructions and processing an incoming data signal.

As used herein, the term "computer program" or "software" is meant generally to include any sequence or human or machine cognizable steps which perform a function. Such program may be rendered in virtually any programming language or environment including, for example, C/C++, C#, Fortran, COBOL, MATLAB™, PASCAL, Python, assembly language, markup languages (e.g., HTML, SGML, XML, VoXML), and the like, as well as object-oriented environments such as the Common Object Request Broker Architecture (CORSA), Java™ (including J2ME, Java Beans, etc.), Binary Runtime Environment (e.g., BREW), and the like.

As used herein, the terms "connection", "link", "transmission channel", "delay line", refer without limitation to a causal link between any two or more entities (whether physical, wired/wireless, or logical/virtual), which enables information exchange between the entities.

As used herein, the term "memory" includes any type of integrated circuit or other storage device adapted for storing digital data including, without limitation, ROM, PROM, EEPROM, DRAM, SDRAM, DDR/2 SDRAM, EDO/FPMS, RLDRAM, SRAM, "flash" memory (e.g., NAND/NOR), memristor, and PSRAM.

As used herein, the terms "microprocessor" and "digital processor" are meant generally to include all types of digital processing devices including, without limitation, digital signal processors (DSPs), reduced instruction set computers (RISC), general-purpose (CISC) processors, microprocessors, gate arrays (e.g., FPGAs), PLDs, reconfigurable compute fabrics (RCFs), array processors, secure microprocessors, and application-specific integrated circuits (ASICs). Such digital processors may be contained on a single unitary IC die, or distributed across multiple components.

As used herein the terms "pulse pattern", "pattern of pulses", or "pattern of pulse latencies" are meant generally and without limitation to denote a group of pulses, arranged (in space and time) in a manner that is recognizable at a predetermined level of statistical significance.

As used herein, the terms "pulse", "spike", "burst of spikes", and "pulse train" are meant generally to refer to, without limitation, any type of a pulsed signal, e.g., a rapid change in some characteristic of a signal, e.g., amplitude, intensity, phase or frequency, from a baseline value to a higher or lower value, followed by a rapid return to the baseline value, and may refer to any of a single spike, a burst of spikes, an electronic pulse, a pulse in voltage, a pulse in electrical current, a software representation of a pulse and/or burst of pulses, a software representation of a latency or timing of the pulse, and any other pulse or pulse type associated with a pulsed transmission system or mechanism.

As used herein, the terms "pulse latency", "absolute latency", and "latency" are meant generally to refer to, without limitation, a temporal delay or a spatial offset between an event (e.g., the onset of a stimulus, an initial pulse, or just a point in time) and a pulse.

As used herein, the terms "pulse group latency", or "pulse pattern latency" refer to, without limitation, an absolute latency of a group (pattern) of pulses that is expressed as a latency of the earliest pulse within the group.

As used herein, the terms "relative pulse latencies" refer to, without limitation, a latency pattern or distribution within a group (or pattern) of pulses that is referenced with respect to the pulse group latency.

As used herein, the term "pulse-code" is meant generally to denote, without limitation, information encoding into a patterns of pulses (or pulse latencies) along a single pulsed channel or relative pulse latencies along multiple channels.

As used herein, the term "wireless" means any wireless signal, data, communication, or other interface including without limitation Wi-Fi, Bluetooth, 3G (e.g., 3GPP, 3GPP2, and UMTS), HSDPA/HSUPA, TDMA, CDMA (e.g., IS-95A, WCDMA, etc.), FHSS, DSSS, GSM, PAN/802.15, WiMAX (802.16), 802.20, narrowband/FDMA, OFDM, PCS/DCS, Long Term Evolution (LTE) or LTE-Advanced (LTE-A), analog cellular, CDPD, satellite systems such as GPS, millimeter wave or microwave systems, optical, acoustic, and infrared (i.e., IrDA).

Overview

The present invention provides, in one salient aspect, improved apparatus and methods for polychronous encoding and multiplexing in neuronal prosthetic devices.

In one embodiment of the invention, a precise spike-timing code is utilized to achieve higher data transmission rate. An exemplary encoding apparatus comprises an encoder that is configured to receive an input signal from an image sensor (such as a charge-coupled device (CCD) or a complementary metal-oxide-semiconductor (CMOS) active pixel sensor device, and to transmit encoded data via multiple transmission channels. The encoder utilizes a precise time base (that is common between different channels), and encodes information into a patterns of pulses that are time-locked to each other but not necessary synchronous. Such pulses are called polychronous (see Izhikevich, E. M. Polychronization: Computation With Spikes. Neural Computation, 2006, 18, 245-282), as shown in FIG. 1. Such patterns of polychronous pulses are referred to as polychronous patterns or polychronous pulse groups. Such pulse groups are the basis of the polychronous code that has even greater information capacity and multiplexing capability than synchronous patterns, because the code uses the relative timing of pulses as an additional variable.

In one implementation, a pulse delay encoding is employed in order to multiplex signals from different sensing elements onto transmission channels, and to generate precise pulse-timing patterns. In another implementation, banks of basis spatial filters are employed to project (partition) the incoming visual signal onto a set of basis projections prior to multiplexing. In one variant, banks of spatio-temporal filters are utilized when the input signals exhibit temporal variability.

In another aspect of the invention, the precise pulse-timing patterns are utilized in a retinal prosthetic device in order to increase data transmission capacity, and to create prosthetic devices to deliver richer (higher-resolution) signals using fewer stimulation electrodes compared to presently available approaches.

In another implementation, the polychronous encoding scheme described here is used in a generalized neuronal prosthetic devices that benefit from an increased transmission bandwidth in order to deliver rich sensory information into the brain via a smaller number of stimulating electrodes.

Embodiments of the polychronous encoding and multiplexing of visual information functionality are useful in a variety of robotic electronic devices and computer vision systems requiring object recognition functionality.

DETAILED DESCRIPTION OF EXEMPLARY EMBODIMENTS

Detailed descriptions of the various embodiments and variants of the apparatus and methods of the invention are now provided. Although certain aspects of the invention can best be understood in the context of the conversion of visual input into polychronous pulse pattern output and subsequent data transmission to the RGCs via stimulating electrodes, embodiments of the invention may also be used for processing of other sensory signals of other, non-visual modalities, including various bands of electromagnetic waves (e.g., infrared, etc.) and pressure (e.g., sound, tactile) signals, and chemical signals (e.g., odor, taste).

Embodiments of the invention may be for example deployed in a hardware and/or software implementation of a computer-vision system, provided in one or more of a prosthetic device, robotic device and any other specialized visual system. In one such implementation, an image processing system may include a processor embodied in an application specific integrated circuit ("ASIC"), which can be adapted or configured for use in an embedded application such as a prosthetic device.

Exemplary Encoding Apparatus

Referring now to FIGS. 1 through 5A, exemplary embodiments of polychronous pulse-code encoding apparatus and methods of the invention are described. In one embodiment, the apparatus and methods encode each object (or a portion of an object or a visual feature) into a pattern of pulses and the timing of the occurrence of the pattern as described in detail below.

It is known in the field of neuroscience that neurons generate action potentials, often called "spikes", "impulses", or "pulses", and transmit them to other neurons. Such pulses are discrete temporal events, and there can be many pulses per unit of time. Conventionally, a stereotypical burst of a few spikes is often considered to be a pulse (also referred to as the "complex spike").

Polychronous Pulse Groups

In one aspect of the invention, the encoding apparatus utilizes a precise time base (that is common between different channels), and encodes information into a patterns of pulses that are time-locked to each other (but not necessary synchronous). FIG. 1 illustrates one example of synchronous (106), non-synchronous (114), and polychronous (116) pulse patterns that utilize two transmission channels (102, 104). In another variant (not shown), a single transmission channel is used in conjunction with a reference time base, such as a periodic clock signal is used instead.

The synchronous pulse transmissions (106) comprise pulse groups 108, 110, 112 that appear in synchronization on both transmission channels 102, 104. The synchronous pulse group 108 contains two distinct time delays (dt1, dt2), and therefore is capable of transmission of two bits of information.

Appearance of pulses and or pulse groups on the channels 102, 104 at undetermined times with respect to each other (or a reference event) corresponds to the non-synchronous (or asynchronous) pulse transmission 114. Such transmissions do not imply a reproducible time-locking pattern, but usually describe noisy, random, non-synchronous events, such as data communication at random intervals.

Polychronous pulse transmissions (such as transmissions 116 in FIG. 1) comprise pulses that appear on two channels (102, 104) at predetermined time intervals with respect to a reference event (such as marked by the vertical dashed line 119).

In polychronous patterns, such as shown by the pulse groups 118 of FIG. 1, there is a predetermined relationship between the pulses, and all of the pulses within the polychronous group 118 appear at predetermined time intervals dt3-dt6. Hence, the polychronous transmissions of four pulses carry 4 bits of information, compared to the two bits carried by the synchronous pulse group 106. The polychronous pulse structure 120 shown in FIG. 1 comprises two polychronous pulse groups 118 that are detectable by a variety of decoding techniques, such as, for example, correlation, matched filter, or coincidence detection coupled with a variable delay.

Figure 1A:
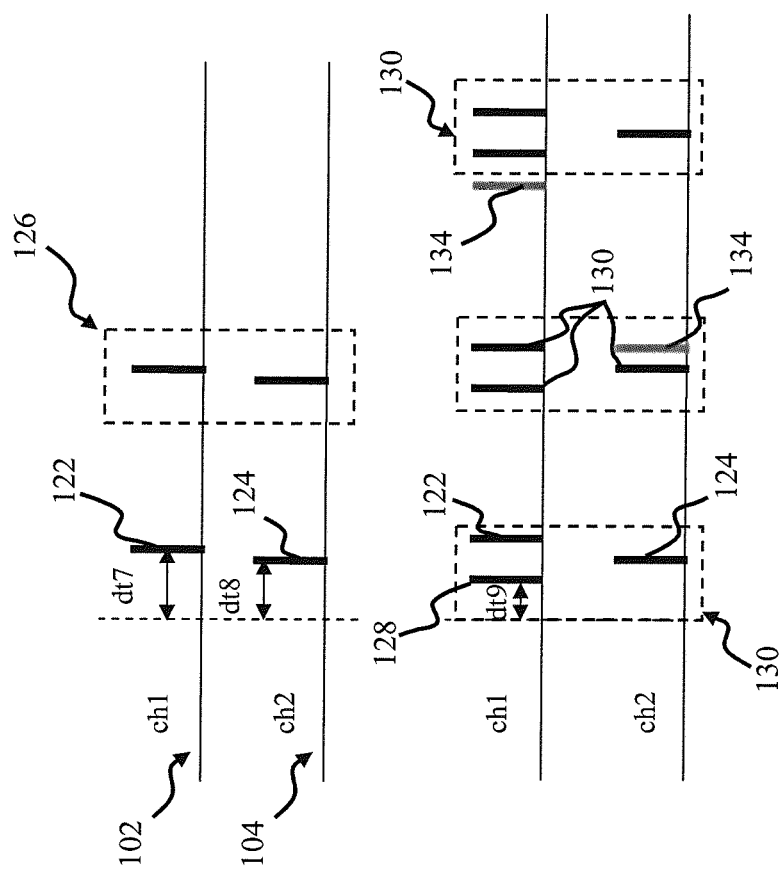
FIG. 1A is a graphical illustration of polychronous pulse groups according to one embodiment of the invention.

FIG. 1A shows other exemplary polychronous pulse patterns useful with the invention. Pulses 122, 124 are generated on the two channels 102, 104, respectively, at predetermined times d7, dt8, all referenced to a common time event. The pulses 122, 124 form the polychronous pattern 126 that may be repeated as shown in FIG. 1A. Another polychronous pattern 130 is comprised of two pulses 122, 128 on the first channel 102 and the pulse 124 on the second channel 104, all generated at predetermined time intervals dt7, dt8, dt9. The pattern 130 is repeated several times with additional randomly appearing pulses 134, which are considered as noise and are removed during processing. The deterministic structure of the polychronous pulse pattern, as characterized by the predetermined pulse timing on different channels that is referenced to the common event, aids in noise removal using e.g., methodologies described below.

Polychronous patterns (such as, for example, the patterns 126, 130 of FIG. 1A) form a basis of the polychronous code that provides greater information capacity and multiplexing capability compared to synchronous patterns, because the polychronous pulse patterns allow the use of pulse timing (such as time delays dt7, dt8, dt9, for example) as an additional variable for data transmission.

Figure 2:
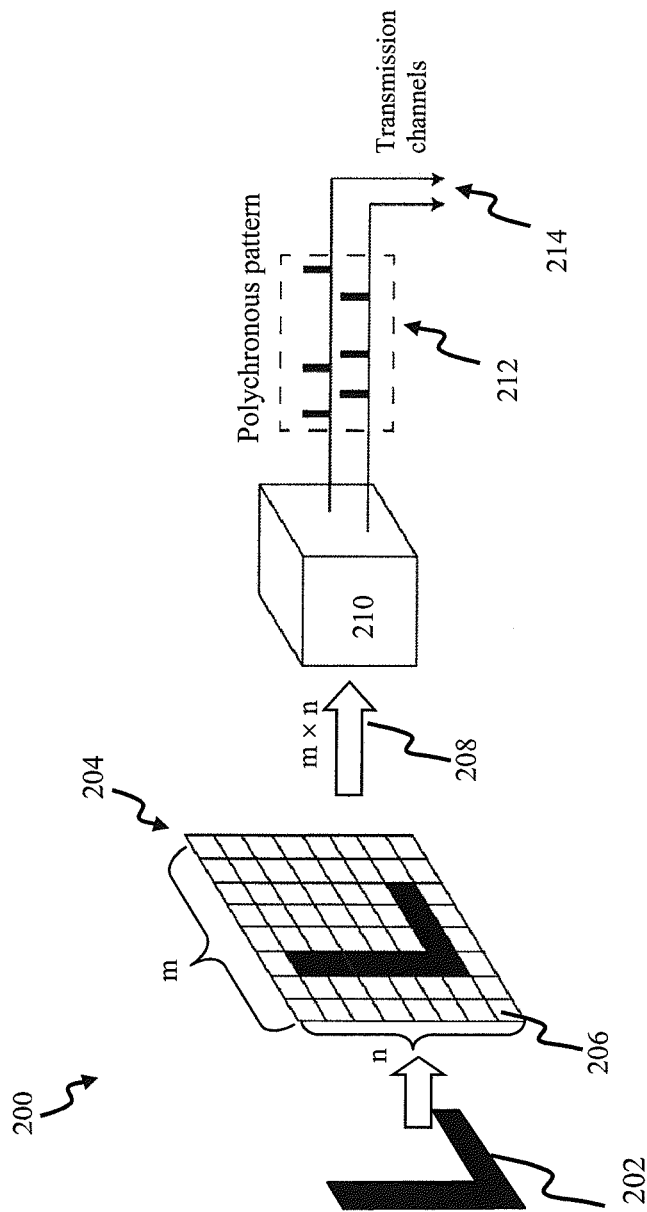
FIG. 2 is a block diagram illustrating an exemplary encoding apparatus according to one embodiment of the invention.

One embodiment of the invention that utilizes polychronous encoding using pulse delays is shown and described below with respect to FIG. 2. An object 202 (such as a letter 'L', although any other visual feature can be used here, such as an edge or a "blob") is placed in a field of view of a visual sensing device, such as a charge-coupled device (CCD) or a complementary metal-oxide-semiconductor (CMOS) active pixel sensor. The visual input signal from the object is captured by light detectors inside the visual sensor, which produce a two-dimensional m×n matrix of pixels 204. The pixel matrix comprises a representation of various object features (such as plurality of edges) and parameters (size, orientation). In the embodiment of FIG. 2, each pixel 206 within the matrix 204 carries a value corresponding to bright or dark areas of the object as represented by the white and the black squares, respectively. In another implementation, each pixel 206 comprises an 8-bit red-green-blue (RGB) three-color model digitized value (e.g., refreshed at a suitable frame rate, for example 10-30 Hz). It will be appreciated by those skilled in the art that the above image parameters are merely exemplary, and many other image representations (e.g., bitmap, cyan-magenta-yellow- and key (CMYK) four color model, n-bit gray scale, etc.) are equally applicable to, and useful with, the present invention. In yet another implementation, the pixel matrix provides a suitably conditioned (amplified, impedance matched and/or filtered) analog output from the light sensors.

The visual sensor output 208 is encoded by the encoder apparatus 210 into polychronous patterns of pulses 212, which are transmitted via transmission channels 214. In one approach, the transmission channels comprise the stimulating electrodes (and accompanying analog signal conditioning circuitry) that couple the encoder to the retinal ganglion cells (or other receptors in retina or in the brain), and stimulate the desired pattern of spikes within the RGCs.

When electrodes are inserted into nervous tissue, pulses of current injected via the electrodes evoke electrical responses in the tissue. A strong brief pulse of current often results in one or more pulses induced in the neurons in the tissue proximal to the electrode. In order to evoke a reliable response in one or a small subset of neurons next to the tip of the stimulating electrode, appropriate conditioning and/or waveform shaping of the stimulating signal may be required. For the purposes of the present discussion, it is assumed that the stimulating signal waveform is adequately configured in order to evoke the desirable pattern of firing in the stimulated neurons.

In another approach, the transmission channels comprise data links that deliver polychronous pulses to a computerized proceeding apparatus.

Delay-Based Encoding

Figure 3:
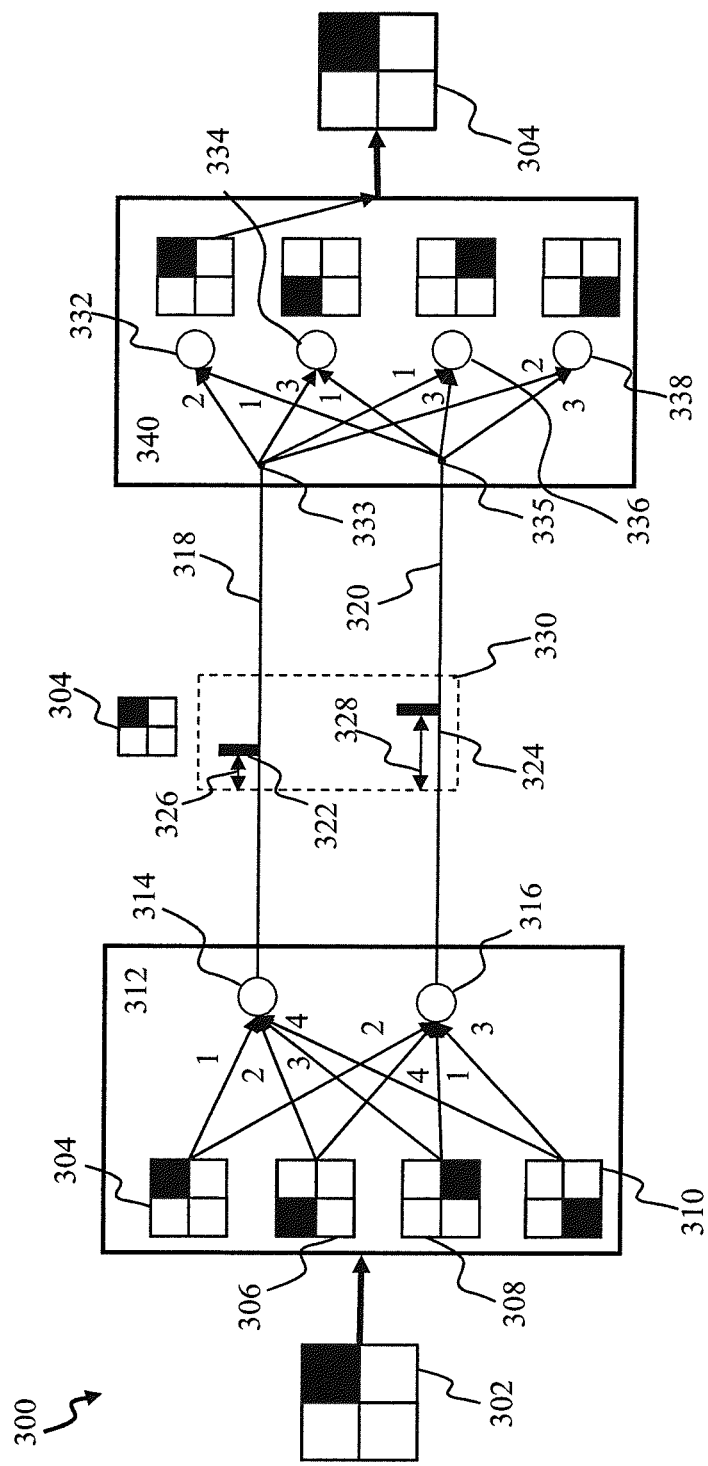
FIG. 3 is a block diagram illustrating visual signal encoding and decoding using pulse latencies according to one embodiment the invention.

In another implementation, the encoding apparatus 300 utilizes a delay-based approach in order to encode the input as illustrated and described with respect to FIG. 3. The encoding apparatus 300 uses delay-transmission lines to convert visual input signal information into polychronous pulse patterns. The exemplary encoding apparatus 300 comprises two transmission channels 318, although other numbers of channels may be used. The input visual pixel matrix (such as the matrix 204 in FIG. 2) is partitioned into two-by-two blocks of pixels, such as the pixel block 302. The visual input signal appears at a time t0, which acts as a reference for all subsequent pulsed events. The encoder apparatus 300 comprises two pulse-generating units, also referred to as the encoder nodes 314, 316. Each pixel in the grid 302 evokes a unique pattern of polychronous pulses in the pulse-generating units 314, 316, which generate pulses based on predetermined delay values. In the embodiment of FIG. 3, dark pixels correspond to a logical value of "one" and white pixels correspond to a logical value of "zero". Other nomenclatures (such as the inverse, or n-level) may be used as well. The encoder delays are configured based on the position of the dark pixel within the grid (as shown by pixel grids 304-310) and the path to the detector node 314, 316. In FIG. 3, the delays are labeled by numerals 1-4, next to the arrows linking the pixel grids 304-310 and the pulse generating units.

For example, if only the top right pixel is active, as in the grid 304, the encoder generates a polychronous pattern 330 along the transmission channels 318, 320. The pulse pattern 330 comprises two pulses (one per each channel) generated with the predetermined delays 326, 328. The delays 326, 328 shown in the example in FIG. 3 are 1 and 2 time units respectively. Here, the time units refer to arbitrary time units, comprising e.g., milliseconds, or units of time of the numerical solver, or units of the global clock).

The pulse pattern 330 is received by a decoding apparatus 340, which comprises two 1-to-4 switching nodes 333, 335 coupling of the transmission channels 318, 320 to the detector nodes 332-338. The detection apparatus 340 applies predetermined delay compensation to the received input. The values of the delay compensation are shown in FIG. 3 as numerals 1-4 next to the arrows linking the nodes 333, 335 and the detectors 332-338.

Each of the detectors 332-338 is configured to receive input each of the transmission channels 318, 320, and use the received input pulses to decode information about the stimulus objects by acting as a coincidence detector. For example the detector node 332, initially in a zero (FALSE) state, transitions to a 'TRUE' state and generates a pulse output if the received pulses are coincident (or nearly coincident within some allowable jitter or tolerance). If the received pulses are not coincident, the detector node 332 remains in the zero state. It will be appreciated by those skilled in the art that the above coincident detector can be implemented using many existing neuronal models, including e.g., the integrate-and-fire model, Hodgkin-Huxley model, FitzHugh-Nagumo model, or quadratic integrate-and-fire model, as well as others.

Figure 3A:
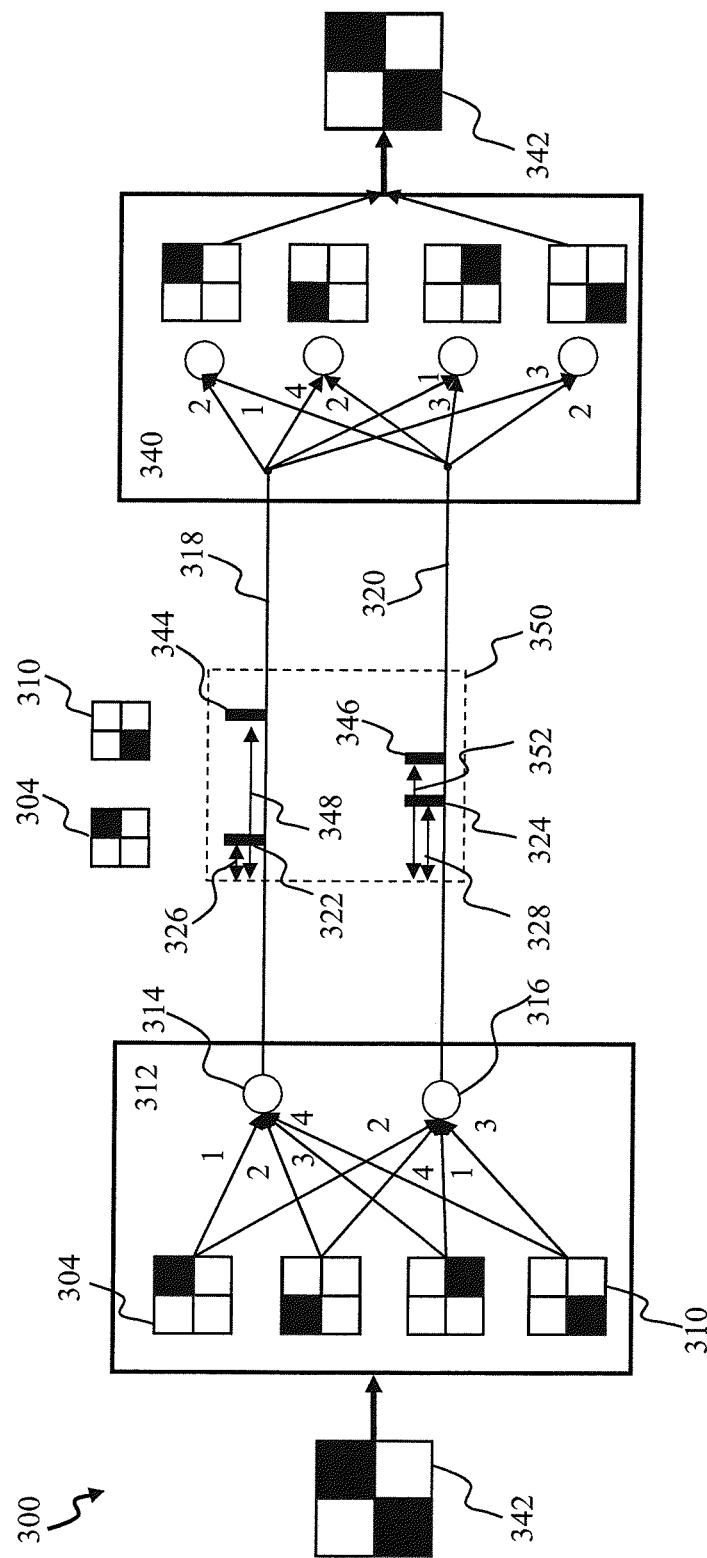
FIG. 3A is a block diagram illustrating visual signal encoding and message multiplexing using pulse latencies according to a one embodiment the invention.

In the example shown in FIG. 3, the detector 332 receives a coincident pulse pair, and generates the detection signal, causing the detection apparatus 340 to report detection of the pixel pattern 303 at its output. All remaining detectors 334-338 remain in their previous states. In another variant comprising more than two transmission channels, the detectors 332-338 generate detection signals whenever they receive two or more coincident pulses FIG. 3A depicts exemplary encoder operation in response to a pixel grid 342 comprising two active pixels, located at the top right and the bottom left of the pixel grid. As shown in FIG. 3A, in addition to the encoder generating the pulses 322, 324 with delays of 1 and 2 respectively (corresponding to the pixel pattern 304), the encoder generates pulses 344, 346 with delays 348, 352 of 4 and 3, respectively. The resulting polychronous pulse pattern is depicted in the dashed box 350 of FIG. 3A. Notice that the pulse pattern 350 is a superposition of two polychronous patterns—one for the first pixel 304, and the other for the second pixel 310. Thus, the pulse pattern 350 conveys independently two different messages using pulse multiplexing.

In another embodiment, a distinct polychronous patterns are designated in order to encode conjunctions of input signals. Certain conjunctions, referred to as the higher-order features, correspond to, for example, intersections of horizontal and vertical lines forming corners of various orientations, etc. are encoded by their specific polychronous patterns.

Figure 3B:
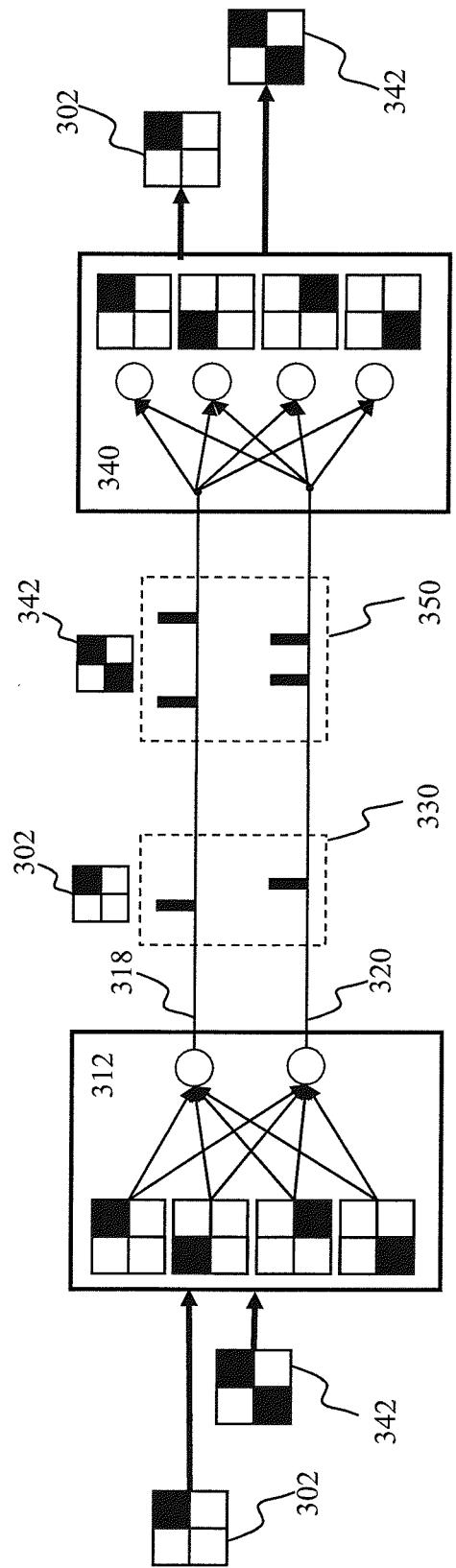
FIG. 3B is a block diagram illustrating encoding and decoding of multiple objects using pulse latencies according to one embodiment the invention.

Referring now to FIG. 3B, exemplary encoding, transmission, and decoding of multiple input pixel grids (or pixel frames) is shown. The encoder 312 receives two separate pixel grids 302, 342 and encodes each grid into a separate polychronous group of pulses (330, 350, respectively). The pulse groups 330, 350 are transmitted from the encoder 312 to the decoder apparatus 340. The decoder decodes the received pulse groups to recover the original pixel grids 302, 342.

Exemplary embodiment of FIGS. 3-3B illustrate to encoding and transmission of 4-bit binary input via 2 transmission channels. This represents a doubling of data throughput/per channel, compared to the presently available solutions that utilize banks of independent transmission channels. Although a 2-by-2 pixel grid is shown in FIGS. 3-3B, it is appreciated by those skilled in the arts that higher density implementations can readily be constructed using the principles of the invention described above.

As it applies to the exemplary embodiments of FIGS. 3-3B, channel information capacity is typically limited by the ability of the encoder unambiguously encode and transmit, and the decoder to unambiguously receive and decode, adjacent pulse pairs without causing pulse to pulse interference, also referred to as the inter-symbol interference or ISI. For a typical pulse of duration T, the maximum pulse rate is limited to less than M=1/T pulses per second (s) (or bits per s (bps). Higher bit rates may be achievable using pulse shaping techniques.

A polychronous encoder, comprising N encoding elements coupled to N output channels (with each carrying pulses at M discrete time intervals), has data capacity of $2^{\{N \times M\}}$ different polychronous patterns to encode $2^{(N \times M)}$ different messages. This number is exponentially more than the number of messages ($2^N$) that can be encoded using the synchronous patterns (as demonstrated by Meister, 1996, Meister and Berry, 1999, and Schnitzer and Meister, 2003) or the number of messages ($M^N$) using the rank-order coding (Van Rullen and Thorpe, 2001). Thus, the encoding apparatus and methods described herein advantageously deliver higher data transmission bandwidth than may be used to deliver higher resolution visual signal (in space, such as higher pixel count, in time (higher frame rate), color, intensity, or luminance contrast representation) using fewer channels.

Depending on the number and density of stimulation electrodes, one can set up the encoding scheme to map more pixels into more pulse-generating units, so as to maximize the information characteristic of the encoder.

When pulse patterns are delivered to the brain via stimulating electrodes, they evoke polychronous firing of action potentials (also called spikes or pulses) in neurons. Since the brain has neuronal fibers with different conduction delays, it is configured to adaptively adjust (learn) the neuronal network in order to decode such polychronous code, and extract the transmitted information.

It is established that the human brain has multiple redundant synaptic connections with a diversity of conduction delays and experience-dependent plasticity, thereby enabling a person to recognize different polychronous patterns by learning and adjusting synaptic strength or the conduction delays. Similarly, the decoder 340 disclosed herein is configurable to adaptively to recognize the polychronous patterns by adjusting the delays or transmission characteristics of the connections onto its pulse-generating units 333-338.

Another embodiment of the present invention comprises a visual sensor with a number of pixels that is substantially greater (by, for example a factor of 10) than the number of pulse-generating units. The pulse-generating units (that are similar to the encoder nodes 314, 316) are configured to generate pulses based on the state of pixels that are proximal to each other, so that there is a continuity and locality of the transformation from the pixel space to the pulse space. Such configuration facilitates learning and decoding of the polychronous patterns by the nervous system.

Filter-Based Encoding

In another aspect of the invention, a set of basis filters is used by the encoder in encoding the sensory input signal into polychronous pulse patterns as shown and described below with respect to FIG. 4. The encoding sequence is divided into two stages; during the first stage, a sensory input (such as the pixel grid 302 described above with respect to FIG. 3) is received by a bank of filters 412 to extract various features. The filter bank comprises a set of basis filters, e.g. $\{F_i; i=1:4\}$, denoted by the designators 404-410, respectively, that are configured to determine a projection of the input sensory signal pattern onto four filter components according to the following expression:

$$f_i = \int I(x) F_i(x) dx. \quad \text{(Eqn. 1)}$$

In some embodiments, it might be desirable to have a set of orthogonal filters; i.e., filters satisfying the orthogonality condition:

$$\int F_i(x) F_j(x) dx = \begin{matrix} 1, i = j \\ 0, i \neq j \end{matrix}. \quad \text{(Eqn. 2)}$$

The integration in Eqns. 1-2 is performed with respect to a spatial vector-variable x, which describes a horizontal and/or vertical dimension of the pixel grid 302.

At the second stage, each of the basis filter projection values $f_i$ is used by the encoder 416 to determine the presence of the active pixel (or a feature such as the active pattern of pixels corresponding to the filter $F_i$), and to construct a corresponding polychronous pattern $P_i$. In one approach, a binary determination algorithm is uses such that if the value of the projection $f_i$ exceeds a certain threshold T, then the output contains $P_i$ note the polychronous pulse pattern 422 generated by the pulse generating nodes 418, 420 of the encoder. Table 1 below provides an exemplary relationship between different filter projections and the corresponding pixel location and encoder delays.

TABLE 1

| Basis filter | Basis projection | Polychronous pattern | Pixel location (row, column) | Encoder delay |
|---|---|---|---|---|
| $F_1$ | $f_1$ | $P_1$ | 1, 2 | 1, 2 |
| $F_2$ | $f_2$ | $P_2$ | 2, 2 | 2, 4 |
| $F_3$ | $f_3$ | $P_3$ | 1, 1, | 3, 1 |
| $F_4$ | $f_4$ | $P_4$ | 2, 1 | 4, 3 |

Figure 4:
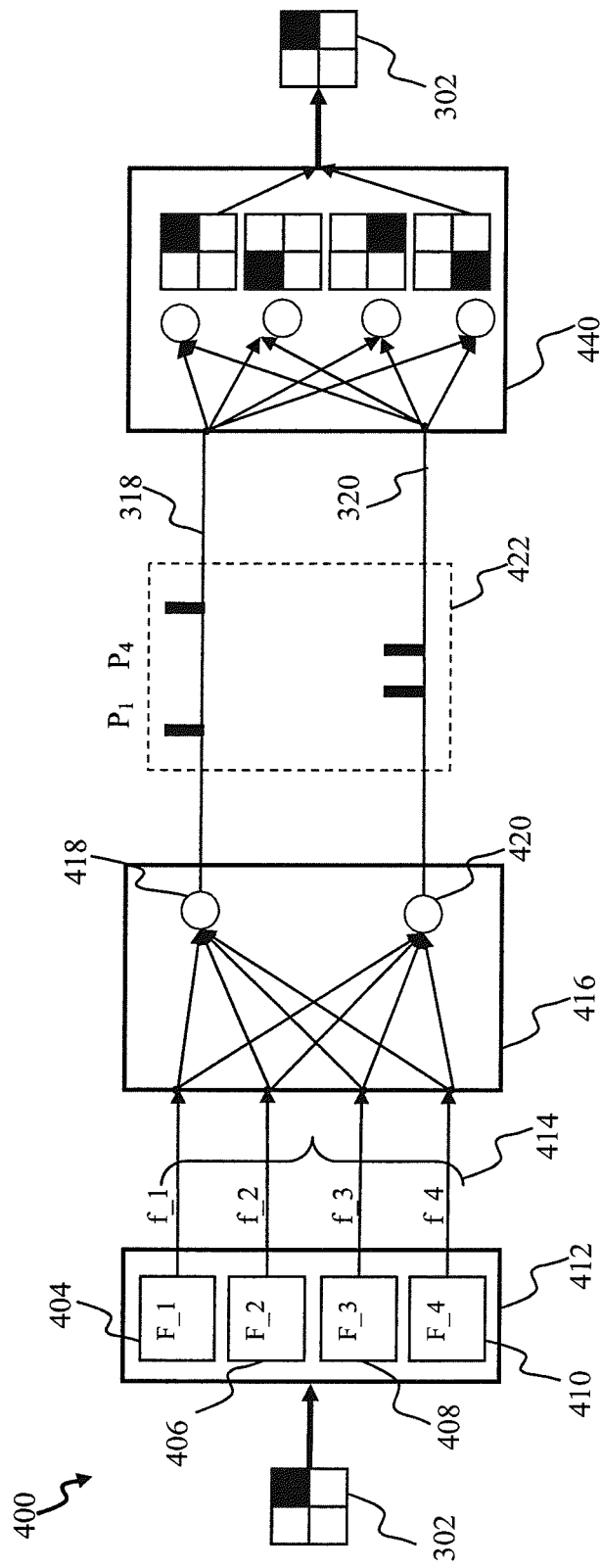
FIG. 4 is a block diagram illustrating visual signal encoding, decoding and message multiplexing using a bank of filters according to one embodiment the invention.

As shown in FIG. 4, the pixel grid 302 comprising an active pixel in the first row and second column evokes the polychronous pattern $P_i$, with the corresponding delay values of 1, 2, which are used by the encoder nodes 418, 420, respectively.

In another variant, an analog basis projection discrimination algorithm is used, such that the value of the filter projection $f_i$ determines the timing (for example, the group delay) of the appearance of the polychronous pulse pattern 422. The group delay is defined herein as a time interval that is common to all pulses within the pulse group as referenced to an event (such as, for example, an appearance of the sensory input). In one variant, the pulse pattern $P_i$ is considered not present when the group delay exceeds a predetermined maximum allowable value. When multiple variables basis filter projection (for example $f_1$ and $f_3$) satisfy the condition of Eqn. 2, the encoder 416 produces a pulse pattern comprised of a superposition of several respective polychronous patterns $P_1$, $P_3$), thereby producing a multiplexed pulse pattern.

The embodiment in FIG. 2 corresponds to the bank of binary filters $F_i(x)$ as in 211-214 (black corresponds to the value of one, and white corresponds to the value of zero) and $P_1=(1,2)$, $P_2=(2,4)$, $P_3=(3,1)$, and $P_4=(4,3)$ with binary determination of the presence of the polychronous pattern $P_i$ in the output based on the nonzero value of the corresponding projection $f_i$. Notice that the pattern 242 is a superposition of $P_1$ and $P_4$. Superposition of two polychronous patterns is a new polychronous pattern.

In another embodiment, not shown, the sensory input I (such as the input pixel grid 302) comprises a temporal component I=I(x, t). Accordingly, a bank of spatio-temporal filters that is filters in the general form of $F_t$ (x, t), is used.

Exemplary Method of Encoder Operation

Figure 5:
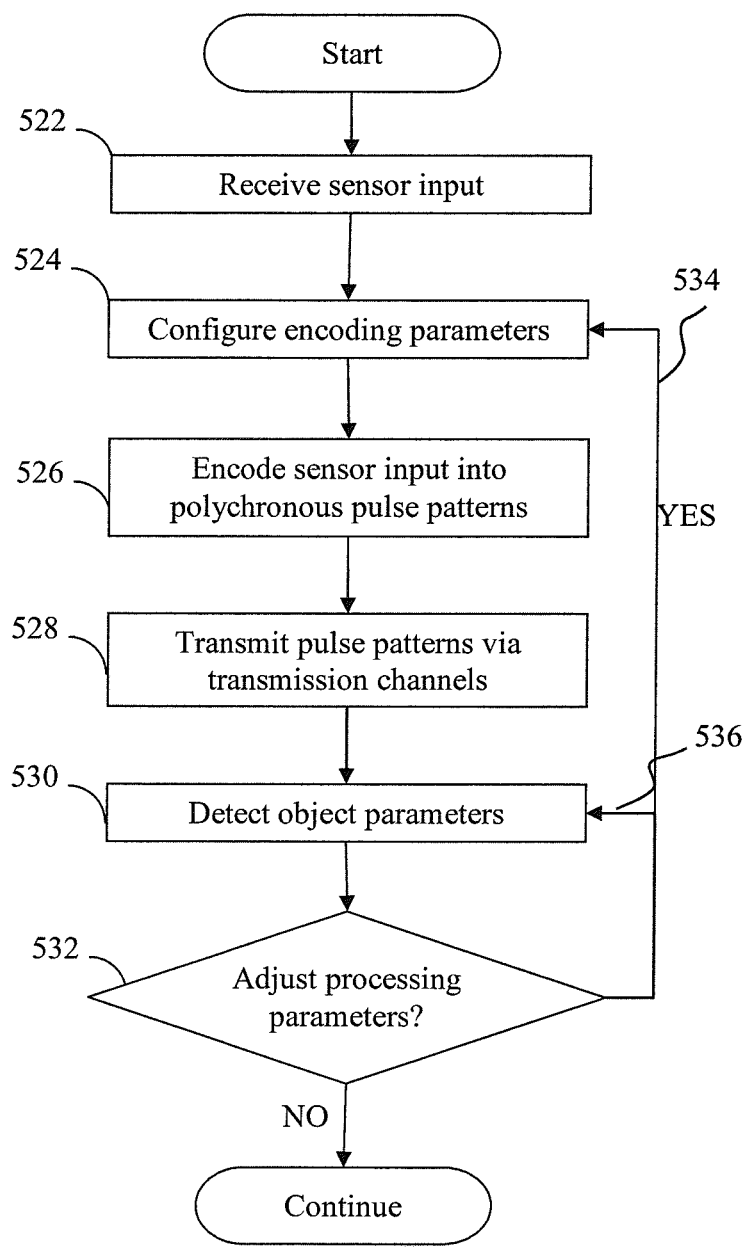
FIG. 5 is a logical flow chart illustrating one exemplary embodiment of the method of encoding and decoding of objects.

In another aspect of the invention, a method of encoder apparatus operation, described in detail with respect to FIG. 5, allows for adaptive adjustment of the encoding parameters (such as encoding of the information from the pixel space to polychronous pulse groups).

At step 522 of the method 500 of FIG. 5, a sensory input corresponding to an object of interest (such as a frame of pixels 204 or a digitized image representing the object 202) is received by the encoding apparatus, such as, for example the 210 of encoder of the apparatus 200 in FIG. 2. At step 524, the encoder 210 configures encoding parameters corresponding to an initial encoder state. At step 526, the sensory input 204 is encoded into a polychronous pattern of pulses (for example pattern 212), and the encoder output is transmitted at step 528 to the destination via transmission channels (such as the channels 214 of FIG. 2). In one implementation, the destination comprises RGCs of a vertebrate nervous system. In another implementation, encoded pulse data are transmitted to computerized image processing apparatus, comprising a plurality of pulse detectors.

At step 530, the received polychronous pulse patterns are analyzed, and detection of object features (such as, for example, different edges of the object 202) is performed. Based on the detection results (such as for example detection score comparison to a preset threshold, timing delay, etc) at step 532 a feedback signal 534 may be provided to the encoder in order to adaptively adjust specific aspects of the encoding and/or parameters of the transmission channels (such as the channels 214 of FIG. 2). In one implementation, the feedback comprises a verbal or other feedback from a patient wearing the prosthetic device. For example, the temporal span of the polychronous pattern (i.e., the average time between the first and the last pulse in the patterns) set initially to large values, are gradually decreased until the patient stops reporting improvements in perception of the sensory signals. In another variant, the number of pulses per stimulating electrodes is adjusted. In yet another variant, the complexity of polychronous patterns (the number of channels that each polychronous pattern spans) is adjusted, or the set of spatiotemporal filters is adjusted, or a combination thereof is adjusted.

In yet another variant, the feedback signal 534 comprises one or more parameters related to the detector state (detection score, detector state adjustment, detection confidence) that are received by the encoder in order to determine if encoding and/or transmission channel adjustment is required.

In one implementation, the generation of polychronous pulse patterns of FIGS. 3 through 4 is triggered by an internal event, e.g., an internal clock cycle. Alternatively, the trigger may comprise an external event, such as, for example, an appearance of a new input signal (e.g., new visual frame) or sudden change of the input signal (e.g., appearance of new object or feature).

Exemplary Uses and Applications of Certain Aspects of the Invention

Polychronous pulse-coded representations advantageously allow for a very high representation capacity in an object recognition apparatus, as compared with a single message per channel data transmission by individual channels. This is due to, inter alia, the use of pulse timing as additional data encoding parameter, and the ability to multiplex different messages (corresponding to different object features and/or objects) into a single pulse group transmission. Such multiplexing is enabled due to at least in part, polychronous properties of the pulse group, where the relative timing of each pulse set is uniquely determined with respect to a reference event thus enabling unambiguous object decoding using, for example, synchronous detection as described above with respect to FIG. 3. Although not commonly accepted in the neuroscience field, the brain has the capability to learn to decode and correctly interpret such patterns, and the present invention takes advantage of such a capability.

Advantageously, the higher information density achieved by the polychronous encoding allows delivering richer (higher-resolution) signals using fewer stimulation electrodes, compared to presently available approaches.

It will be recognized that while certain aspects of the invention are described in terms of a binary pixel image processing, these descriptions are only illustrative of the broader methods of the invention, and may be modified as required by the particular application. Therefore, polychronous encoding may be applied to encoding of other visual characteristics such as color, transparency, contrast, luminance, or visual motion as well as non-visual sensory inputs signals (e.g., infrared signals or other electromagnetic signals outside the visible spectrum).

It will be further recognized that while certain aspects of the invention are described in terms of retinal prosthetic device, principled of the invention are useful in a wide variety of other sensory prosthetic applications comprising delivery of sensory signals to the brain via a peripheral prosthetic device, such as auditory prosthetics (cochlear), using skin or tongue stimulation, or stimulating nervous tissue inside the brain using wireless connections.

Advantageously, exemplary embodiments of the present invention are useful in a variety of robotics and computer vision devices to efficiently transfer visual and other sensory information from peripheral sensors (e.g., the camera) to the information-processing unit (e.g., artificial nervous system) including without limitation prosthetic devices, autonomous and robotic apparatus, and other electromechanical devices requiring objet recognition functionality. Examples of such robotic devises are manufacturing robots (e.g., automotive), military, medical (e.g. processing of microscopy, x-ray, ultrasonography, tomography), Examples of autonomous vehicles include rovers, unmanned air vehicles, underwater vehicles, smart appliances (e.g. ROOMBA®), etc.

The foregoing descriptions of the invention are intended to be illustrative, and not in any way limiting; those skilled in the art will appreciate that the invention can be practiced with various combinations of the functionalities and capabilities described above, and can include fewer or additional components than described above. Certain additional aspects and features of the invention are further set forth below, and can be obtained using the functionalities and components described in more detail above. These improvements advantageously translate into a system that requires fewer detectors and fewer processing units, compared to the prior art, and that allows taking advantage of the combinatorial richness of the pulse code and the brain's ability to decode and interpret it.

Embodiments of the present invention are further applicable to a wide assortment of applications including computer human interaction (e.g., recognition of gestures, voice, posture, face, etc.), controlling processes (e.g., an industrial robot, autonomous and other vehicles), augmented reality applications, organization of information (e.g., for indexing databases of images and image sequences), access control (e.g., opening a door based on a gesture, opening an access way based on detection of an authorized person), detecting events (e.g., for visual surveillance or people or animal counting, tracking), data input, financial transactions (payment processing based on recognition of a person or a special payment symbol) and many others.

Advantageously, the present invention can be used to simplify tasks related to motion estimation, such as where an image sequence is processed to produce an estimate of the object position (and hence velocity) either at each points in the image or in the 3D scene, or even of the camera that produces the images. Examples of such tasks are: ego motion, i.e., determining the three-dimensional rigid motion (rotation and translation) of the camera from an image sequence produced by the camera; following the movements of a set of interest points or objects (e.g., vehicles or humans) in the image sequence and with respect to the image plane.

In another approach, portions of the object recognition system are embodied in a remote server configured to perform pattern recognition in data streams for various applications, such as scientific, geophysical exploration, surveillance, navigation, data mining (e.g., content-based image retrieval). Myriad other applications exist that will be recognized by those of ordinary skill given the present disclosure.

It will be recognized that while certain aspects of the invention are described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the invention disclosed and claimed herein.

While the above detailed description has shown, described, and pointed out novel features of the invention as applied to various embodiments, it will be understood that various omissions, substitutions, and changes in the form and details of the device or process illustrated may be made by those skilled in the art without departing from the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed:

1. An apparatus configured to transmit a signal to a vertebrate nervous system, the apparatus comprising:
   a processor configured to receive an input signal representative of at least a portion of a visual frame;
   an encoder configured to encode the input signal into a plurality of pulses; and
   a plurality of stimulating electrodes;
   wherein:
      at least a subset of the plurality of pulses is configured in a polychronous pattern comprising at least two non-synchronous pulses;
      information related to the at least the portion of the visual frame is encoded by the processor into the polychronous pattern;
      the polychronous pattern is characterized by a group delay that is common to all pulses within the plurality of pulses, the group delay being determined by a spatiotemporal filter applied to the input signal; and
      wherein the polychronous pattern is adapted for transmission via the plurality of stimulating electrodes operably coupled to the vertebrate nervous system.

2. The apparatus of claim 1, wherein the apparatus comprises at least a portion of a retinal prosthetic device.

3. The apparatus of claim 2, wherein individual ones of the plurality of stimulating electrodes are configured for operable coupling to a receptor of the vertebrate nervous system, the receptor comprising one or more of a retinal ganglion cell and a retinal bipolar cell.

4. The apparatus of claim 2, wherein the encoder is configurable to be adaptively adjusted based at least in part on a feedback signal provided by a host of the prosthetic device.

5. The apparatus of claim 4, wherein:
   the encoding of the input signal into the plurality of pulses is characterized by at least one parameter; and
   the encoder adaptive adjustment is configured to modify the at least one parameter.

6. A sensory input encoding apparatus, comprising:
   a processing apparatus configured to receive and encode a sensory input into a plurality of pulses, the sensory input comprising information indicative of an object characteristic, and the processing apparatus is further configured to encode at least a portion of the plurality of pulses in a first polychronous pattern comprising at least two non-synchronous pulses;
   wherein the first polychronous pattern is characterized by a group delay that is common to all pulses within the plurality of pulses, the group delay configured based at least in part on the sensory input;
   wherein the sensory input comprises a visual input signal; and
   wherein the group delay is based at least in part on an output generated by a spatiotemporal filter using the sensory input.

7. The apparatus of claim 6, wherein the sensory input comprises a frame of pixels.

8. The apparatus of claim 6, wherein the first polychronous pattern is generated responsive to a trigger selected from the group consisting of: (i) a temporal event; (ii) a receipt of the sensory input; (iii) an appearance of an object in the sensory input; and (iv) a timer event.

9. The apparatus of claim 6, wherein the first polychronous pattern is adapted for transmission via a plurality of transmission channels.

10. The apparatus of claim 9, wherein: at least a subset of the plurality of transmission channels is associated with a channel delay configured to effect a coincident arrival of the at least two non-synchronous pulses at a decoder.

11. The apparatus of claim 10, wherein the channel delay is configured based at least in part on the first polychronous pattern.

12. The apparatus of claim 11, wherein the coincident arrival of the at least two non-synchronous pulses at the decoder is configured to indicate presence of the object characteristic in the sensory input.

13. The apparatus of claim 12, wherein:
   the sensory input comprises a plurality of pixels; and
   the coincident arrival of the at least two non-synchronous pulses at the decoder is configured to indicate a presence of the object characteristic within the plurality of pixels.

14. A sensory input encoding apparatus, comprising:
   a processing apparatus configured to receive and encode a sensory input into a plurality of pulses,
   the sensory input comprising information indicative of an object characteristic; and and the processing apparatus being further configured to encode at least a portion of the plurality of pulses in a first polychronous pattern comprising at least two non-synchronous pulses;

wherein the first polychronous pattern is characterized by a group delay that is common to all pulses within the plurality of pulses, the group delay configured based at least in part on the sensory input;

wherein the first polychronous pattern is adapted for transmission via a plurality of transmission channels; and wherein at least a subset of the plurality of transmission channels is associated with a channel delay configured to effect a coincident arrival of the at least two non-synchronous pulses at a decoder.

15. The apparatus of claim 14, wherein the channel delay is configured based at least in part on the first polychronous pattern.

16. The apparatus of claim 15, wherein:
the group delay is configured with reference to an event; and
the coincident arrival of the at least two non-synchronous pulses at the decoder is configured to indicate a presence of the object within the sensory input.

17. The apparatus of claim 16, wherein the event is selected from the group consisting of: (i) a temporal event; (ii) a receipt of the sensory input; (iii) an appearance of an object in the sensory input; and (iv) a timer event.

18. The apparatus of claim 14, wherein the decoder comprises a coincidence detector configured to receive the at least two non-synchronous pulses and to decode the object characteristic responsive to the reception of the at least two non-synchronous pulses.

19. A sensory input encoding apparatus, comprising:
a processing apparatus configured to receive and encode a sensory input into a plurality of pulses,
the sensory input comprising information indicative of an object characteristic; and
and the processing apparatus being further configured to encode at least a portion of the plurality of pulses in a first polychronous pattern comprising at least two non-synchronous pulses;

wherein the first polychronous pattern is characterized by a group delay that is common to all pulses within the plurality of pulses, the group delay configured based at least in part on the sensory input;

wherein the first polychronous pattern is adapted for transmission via individual ones of a plurality of transmission channels; and wherein at least a subset of the plurality of the transmission channels is configurable based on a second polychronous pattern generated prior to the first polychronous pattern.

20. The apparatus of claim 19, wherein the configuration of the subset of the plurality of the transmission channels based on the second polychronous pattern comprises a configuration of a channel delay of the subset of the plurality of the transmission channels.

21. The apparatus of claim 20, wherein the configuration of the channel delay is configured to effectuate a coincident arrival of the at least two non-synchronous pulses at a decoder.

22. The apparatus of claim 21, wherein the group delay is configured with reference to an event selected from the group consisting of: (i) a temporal event; (ii) a receipt of the sensory input; (iii) an appearance of an object in the sensory input; and (iv) a timer event.

23. The apparatus of claim 21, wherein:
the group delay is configured with reference to an event;
the sensory input comprises a visual input; and
the event is configured based on an appearance of an object in the sensory input.

24. The apparatus of claim 23, wherein the coincident arrival of the at least two non-synchronous pulses at the decoder is configured to signify an occurrence of the object characteristic within the sensory input.

* * * * *